United States Patent [19]
Dowell et al.

[11] Patent Number: 6,143,509
[45] Date of Patent: Nov. 7, 2000

[54] PROSTATE SPECIFIC ANTIGEN PEPTIDES AND USES THEREOF

[75] Inventors: Barry Lee Dowell, Mundelein, Ill.; Dominique P. Bridon, San Francisco, Calif.; Xiaoxing Qiu, Gurnee, Ill.; Hans Lilja, Hollviken, Sweden; Timo Petteri Piironen, Turku, Finland; Mauno Antero Vihinen, Helsinki, Finland; Kim Sverker Immanuel Pettersson, Turku, Finland

[73] Assignee: Abbott Laboratories, Abbott Park, Ill.

[21] Appl. No.: 08/595,945

[22] Filed: Feb. 6, 1996

[51] Int. Cl.⁷ .................. G01N 33/574; G01N 33/48; C07K 16/00; C12P 21/08
[52] U.S. Cl. .................. 435/7.23; 435/810; 436/64; 530/387.7; 530/387.9; 530/388.8
[58] Field of Search ................... 435/7.23, 810; 530/387.7, 387.9, 388.26, 388.8, 388.85, 389.7; 436/64, 813

[56] References Cited

U.S. PATENT DOCUMENTS

| | | | |
|---|---|---|---|
| 5,501,983 | 3/1996 | Lilja et al. | 436/518 |
| 5,807,978 | 9/1998 | Kokolus et al. | |

FOREIGN PATENT DOCUMENTS

| | | |
|---|---|---|
| 9201936 | 2/1992 | WIPO. |
| 9403205 | 2/1994 | WIPO. |
| 9420127 | 9/1994 | WIPO. |
| 9503334 | 2/1995 | WIPO. |
| 9640754 | 12/1996 | WIPO. |

OTHER PUBLICATIONS

A. Luderer et al., *Urology*, vol. 46, No. 2, pp. 187–194 (1995).
R. McCormack et al., *Urology*, vol. 45, No. 5, pp. 729–744 (1995).
A. Partin et al., *The Journal of Urology*, vol. 152, pp. 1358–1368 (1994).
D. Bridon et al., *Urology*, vol. 45, No. 5, pp. 801–806 (1995).
T. Chu et al., *The Journal of Urology*, vol. 141, pp. 152–156 (1989).
K. Mitrunen et al., *Clin. Chem.*, vol. 41, No. 8, pp. 1115–1120 (1995).
H. Lilja et al., *Cancer Supplement*, vol. 70, No. 1, pp. 230–234 (1992).
H. Lilja et al., *Urologic Clinics of North America*, vol. 20, No. 4 pp. 681–686 (1993).
A. Christensson et al., *The Journal of Urology*, vol. 150, pp. 100–105 (1993).
H. Lilja et al., *Clin. Chem.*, vol. 37, No. 9, pp. 1618–1625 (1991).
U.–H. Stenman et al., *Cancer Research*, vol. 51, pp. 222–226 (1991).
E. Corey et al., *J. Urology*, vol. 155, pp. 697A (1996).
U.–H. Stenman et al., *The Lancet*, vol. 344, pp. 1594–1597 (1994).
Clinical Chemistry, vol. 43, No. 4, Apr. 1997, Winston US, pp. 575–584, E. Corey et al., "Prostate–specific antigen: characterization of epitopes by synthetic peptide mapping and inhibition studies".
Methods in Enzymology, vol. 178, 1989, pp. 586–611, V. Krchnak et al., "Computer prediction of B–cell determinants from protein amino acid sequences based on incidence of beta–turns".
Clinical Chemistry, vol. 41, No. 10, 1995, Winston US, pp. 1480–1488, Kim Petterson et al., "Free and complexed Prostate–specific–antigen (PSA): in vitro stability, epitope map, and development of immunofluormetric assays for specific and sensitive detection of free PSA and PSA–alpha 1–antichymotrypsin complex".
Biochemical and Biophysical Research Communications, vol. 213, No. 2, Aug. 1995, pp. 888–895, J. Loevgren et al., "Production of recombinant PSA and HK2 and analysis of their immunologic cross–reactivity".
Advances In Clinical Chemistry, vol. 31, 1994, pp. 99–133, A. M. El–Shirbiny, "Prostatic Specific Antigen".
Harlow, et al., in *Antibodies, A Laboratory Manual*, Harlow, ed., Cold Spring Harbor Laboratory, 1988, pp. 72–77.
Christensson, et al., Eur. J. Biochem., vol. 220, 1994, pp. 45–53.

*Primary Examiner*—Yvonne Eyler
*Attorney, Agent, or Firm*—Cheryl L. Becker

[57] ABSTRACT

The present invention relates to peptides which may be used, for example, in the detection of free and complexed Prostate Specific Antigen and thus in the diagnosis of prostate cancer.

15 Claims, 8 Drawing Sheets

```
                  1                                                           48
HK2    IVGGWECEKH SQPWQVAVYS H.GWAHCGGV LVHPQWLTA AHCLK.KNSQ
PSA    IVGGWECEKH SQPWQVLVAS R.GRAVCGGV LVHPQWVLTA AHCIR.NKSV
       |---ABT14------|                 |----ABT13------|
             |----ABT12---------|

50                                                          97
HK2    VWLGRHNLFE .PEDTGQRVP VSHSFPHPLY NMSLLKHQSL RPDEDSSHDL
       |------hK2a--------|                 |------hK2b--------|
PSA    ILLGRHSLFH .PEDTGQVFQ VSHSFPHPLY DMSLLKNRFL RPGDDSSHDL
       |C----ABT4-------|                    |C----ABT6------|
                         |----ABT10----------|
                                             |C----ABT1-----C|

99                                                         145
HK2    MLLRLSEPAK ITDVVKVLGL PT..QEPALG TTCYASGWGS IEPEE..FLR
PSA    MLLRLSEPAE LTDAVKVMDL PT..QEPALG TTCYASGWGS IEPEE..FLT
       |----ABT7---------|                    |C----ABT2------|
                          |----ABT17-------|

146                                                        193
HK2    PRSLQCVSLH LLSNDMCARA YSEKVTEFML CAGLWTGGKD TCGGDSGGPL
PSA    PKKLQCVDLH VISNDVCAQV HPQKVTKFML CAGRWTGGKS TCSGDSGGPL
       |----ABT3--------|                    |----ABT9------|
                |----ABT16-------|
                          |----ABT15-------|

196                                                        237
HK2    VCN....GVL QGITSWGPEP CALP.EKPAV YTKVVHYRKW IKDTIAANP
PSA    VCN....GVL QGITSWGSEP CALP.ERPSL YTKVVHYRKW IKDTIVANP----A|
       |----ABT5---------|                     |----ABT8------|
```

FIG. 1B

```
                          SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:1:

Cys Asn Arg Phe Leu Arg Pro Gly Asp Asp Ser Ser Cys
1               5                  10

(2) INFORMATION FOR SEQ ID NO:2:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:2:

Cys Trp Gly Ser Ile Glu Pro Glu Glu Phe Leu Thr Pro Lys Lys
1               5                  10                  15

Leu Cys (2) INFORMATION FOR SEQ ID NO:3:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:3:

Cys Ala Gln Val His Pro Gln Lys Val Thr Lys Phe Met Leu Cys
1               5                  10                  15

(2) INFORMATION FOR SEQ ID NO:4:
```

```
        (i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:4:

Cys Leu Leu Gly Arg His Ser Leu Phe His Pro Glu Asp Thr Gly
 1               5                  10                  15

Gln Cys (2) INFORMATION FOR SEQ ID NO:5:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:5:

Thr Ser Trp Gly Ser Glu Pro Cys Ala Leu Pro Glu Arg Pro Ser
 1               5                  10                  15

Leu Tyr (2) INFORMATION FOR SEQ ID NO:6:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:6:

Cys Met Ser Leu Leu Lys Asn Arg Phe Leu Arg Pro Gly Asp Asp
 1               5                  10                  15

Ser Cys (2) INFORMATION FOR SEQ ID NO:7:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:7:

Ser Glu Pro Ala Glu Leu Thr Asp Ala Val Lys Val
 1               5                  10

(2) INFORMATION FOR SEQ ID NO:8:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein
```

```
        (xi) SEQUENCE DESCRIPTION: SEQ ID NO:8:

His Tyr Arg Lys Trp Ile Lys Asp Thr Ile Val Ala Asn Ala
1               5                   10

(2) INFORMATION FOR SEQ ID NO:9:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:9:

Ala Gly Arg Trp Thr Gly Gly Lys Ser Thr Cys Ser Gly Asp Ser
1               5                   10                  15

Gly (2) INFORMATION FOR SEQ ID NO:10:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:10:

Ser His Ser Phe Pro His Pro Leu Tyr Asp Met Ser Leu Leu Lys
1               5                   10                  15

(2) INFORMATION FOR SEQ ID NO:11:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:11:

Val Met Asp Leu Pro Thr Gln Glu Pro Ala Leu Gly Thr Thr Cys
1               5                   10                  15

(2) INFORMATION FOR SEQ ID NO:12:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:12:

His Ser Gln Pro Trp Gln Val Leu Val Ala Ser Arg Gly Arg Ala
1               5                   10                  15

Val (2) INFORMATION FOR SEQ ID NO:13:

(i) SEQUENCE CHARACTERISTICS:
         (A) LENGTH: 14 amino acids
         (B) TYPE: amino acid
```

```
            (C) STRANDEDNESS: single
            (D) TOPOLOGY: linear (ii) MOLECULE TYPE: protein (xi) SEQUENCE DESCRIPTION: SEQ ID NO:13:

Pro Gln Trp Val Leu Thr Ala Ala His Ile Arg Asn Lys Ser
1               5                   10

(2) INFORMATION FOR SEQ ID NO:14:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:14:

Val Gly Gly Trp Glu Cys Glu Lys His Ser Gln Pro Trp Gln
1               5                   10

(2) INFORMATION FOR SEQ ID NO:15:

(i) SEQUENCE CHARACTERISTICS:
            (A) LENGTH:19 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:15:

Ser Asn Asp Val Cys Ala Gln Val His Pro Gln Lys Val Thr Lys
1               5                   10                  15

Phe Met Leu Cys (2) INFORMATION FOR SEQ ID NO:16:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:16:

Asp Leu His Val Ile Ser Asn Asp Val Cys Ala Gln Val His Pro
1               5                   10                  15

Gln Lys
```

PROSTATE SPECIFIC ANTIGEN PEPTIDES AND USES THEREOF

BACKGROUND OF THE INVENTION

1. Technical Field

The present invention relates to peptides which may be used, for example, in the detection of free and complexed Prostate Specific Antigen (PSA) and thus in the diagnosis of prostate cancer.

2. Background Information

Prostate specific antigen (PSA) is a low molecular weight glycoprotein of approximately 30 kilodaltons (kD) produced mainly by prostatic glandular epithelial cells. PSA is a member of the human tissue kallikrein gene family, which consists of three genes, hKLK1, hKLK2, and hKLK3. The protein product of these genes are pancreatic-kidney kallikrein (hK1), human glandular kallikrein (hK2) (previously known as hGK-1), and PSA (hK3). PSA is a serine protease and exhibits a chymotrypsin-like specificity cleaving at a hydrophobic residue (see Chu et al., *J. Urol.* 141:152–56 (1989)). The other two kallikreins have trypsin-like specificity. These three genes are located on chromosome 19. The expression of both PSA and hK2 are under androgen control. The protein for hK2 has not been isolated, and its potential clinical utility has not been determined (McCormack et al., *Urology* 45:729–44 (1995); see also copending U.S. patent application Ser. No. 08/394,033).

PSA is produced in the prostate and occurs in high concentrations in prostate and seminal fluid. It also occurs in urine and in serum. The concentration of serum PSA in the normal male increases with age. Increased levels of serum PSA are found in benign prostatic hyperplasia (BPH), prostatitis and prostate cancer. The expression of PSA in most females is negative or very low. While PSA isolated from seminal fluid or prostatic tissue occurs predominately as the 30 kD form of PSA, PSA in the serum occurs in various forms. A small portion of serum PSA occurs as low molecular weight or free PSA. The majority of immunodetectable PSA occurs as a 100 kD complex of PSA and alpha-1-antichymotrypsin (ACT) otherwise known as complexed PSA (PSA-ACT). Another PSA complex formed with alpha-2-macrogobulin is not detectable by current immunoassays. PSA complexes with these protease inhibitors through its serine protease active site. Presumably, the free PSA in serum is inactive PSA, since serum contains an excess of protease inhibitors (McCormack et al., *Urology* 45:729–44 (1995), Partin et al.,*J. Urol.* 152:1358–68(1994), Lilja et al., *Clin. Chem.* 37:1618 (1991), Stenman et al., *Cancer Res.* 51:222 (1991) and WO 92/09136).

Serum PSA has become the most clinically useful tumor marker in prostatic disease. PSA is used to monitor the response to therapy and detect early relapses for prostate cancer. When prostate cancer is treated with radiation, surgery or androgen-deprivation, the serum levels of PSA decrease. The level that they decrease to following therapy is correlated to prognosis and survival. When used following radical prostatectomy, the PSA level following successful treatment should decrease to zero, since the prostate is the only significant source of PSA. This allows PSA to be a very sensitive marker for tumor relapse following surgery. PSA has also been used to help stage patients. It has been shown that PSA level correlates with tumor volume, but is not accurate enough to independently stage the disease; however, PSA level is useful in combination with other clinical and pathological parameters (Partin et al., *J. Urol.* 152:1358–68 (1994)).

A major development in the use of PSA is its application to the early detection of prostate cancer prior to the appearance of clinical symptoms. Prior to the advent of the use of PSA, the digital rectal exam was used (DRE). This method was not very sensitive or specific. In addition, many tumors detected by DRE were too large to cure. The use of PSA in conjunction with DRE as an early detection method has been validated in several clinical studies. Typically, a cutoff of 4.0 ng/mL has been used as the upper limit of normal. Above this level, about 33% of biopsies are positive, while above 10 ng/mL, approximately 67% are positive. PSA levels above a value of 4.0 can be due to prostatitis or benign prostate hypertropy (BPH). Most men over 50 years old have some evidence of BPH. Age-specific reference ranges for PSA have been suggested as a way to improve PSA's use in early detection (Parkin, et al., *J. Urol.* 152:1358–68 (1994)).

Patients with PSA below 4.0 ng/mL with a normal DRE are considered normal, while those above 10 ng/mL are considered likely to have prostate cancer. Therefore, the gray zone is between 4 and 10 ng/mL. Several methods have been devised to improve the specificity of PSA in early detection. They include: 1) the use of age-specific reference ranges, 2) the use of PSA changes over time, 3) the use of PSA density and 4) the use of ratios of PSA forms. It has been shown that the use of ratios of free PSA levels divided by total PSA levels or ratios of PSA-ACT complex levels divided by total PSA levels can improve the specificity of PSA for cancer. This is because the serum of patients with prostate cancer tend to have less free PSA than do the serum of men with BPH (McCormack et al., *Urology* 45:729–44 (1995), Partin et al., *J. Urol.* 152:1358–68 (1994), Lilja et al., *Clin. Chem.* 37:1618 (1991), Stenman et al., *Cancer Res.* 51:222 (1991) Christensson et al., *J. Urol.* 150:100–105 (1993) and WO 92/01936).

The peptides of the present invention will enable the production of antisera necessary to determine the amount of total PSA, free PSA and PSA-ACT complex present in a sample and thus improve the ability of the clinician to distinguish, for example, between BPH and prostrate cancer in a patient. The proper course of treatment may then be undertaken. This use and other uses of the present peptides will be described in further detail below.

All U.S. patents and publications referred to herein are hereby incorporated in their entirety by reference.

SUMMARY OF THE INVENTION

The present invention relates to a purified peptide comprising an amino acid sequence of approximately 10–20 residues which is identical to the amino acid sequence of a region of PSA and comprises one or more amino acids nonidentical to the amino acid sequence of hK2. Alternatively, the sequence of the peptide may be identical to the sequence of both the amino acid sequence of a region of PSA and hK2. These peptides may, for example, be selected from the group consisting of ABT1 (SEQ. ID. No:1), ABT2 (SEQ. ID. No:2) ABT3 (SEQ. ID. No:3), ABT4 (SEQ. ID. No:4), ABT5 (SEQ. ID. No:5), ABT6 (SEQ. ID. No:6), ABT7 (SEQ. ID. No:7), ABT8 (SEQ. ID. No:8), ABT9 (SEQ. ID. No:9), ABT10 (SEQ. ID. No:10), ABT11 (SEQ. ID. No:11), ABT12 (SEQ. ID. No:12), ABT13 (SEQ. ID. No:13), ABT15 (SEQ. ID. No:15) and ABT16 (SEQ. ID. No:16).

Furthermore, the present invention also includes an antibody specific for free PSA produced in response to immunization by a peptide of the present invention. Examples of such peptides are ABT6 and ABT1. Antibodies against these peptides may be monoclonal or polyclonal.

Additionally, the present invention relates to an antibody specific for total PSA produced in response to immunization by a peptide selected from the group consisting of ABT4, ABT14 and ABT16. Again, such antibodies may be monoclonal or polyclonal.

Moreover, the present invention also encompasses a method for detecting PSA in a test sample suspected of containing PSA. This method comprises the steps of: a) contacting the test sample with an antibody or fragment thereof which specifically binds to at least one site on a peptide or antigen for a time and under conditions sufficient to allow for the formation of antigen/antibody complexes; b) adding a probe antibody to the resulting antigen/antibody complexes for a time and under conditions sufficient to allow the probe to bind to bound antigen, wherein the probe binds to a second site on the peptide or antigen; and c) determining the amount of bound probe and thus the amount of PSA in the test sample. The PSA peptide or antigen comprises an amino acid sequence of approximately 10–20 residues wherein said sequence is identical to the amino acid sequence of a region of PSA and comprises one or more amino acids nonidentical to the amino acid sequence of hK2. For example, the peptide or antigen may be selected from the group consisting of ABT2, ABT4, ABT6, ABT1, ABT7, and ABT16. The antibody of step (a) may be attached to a solid phase, and the antibody of step (c) may labelled with a radioactive isotope. Additionally, one antibody may be specific for free PSA and the other antibody may be specific for total PSA, or both antibodies may be specific for total PSA.

The present invention also includes another method of detecting PSA in a test sample suspected of containing PSA. The method comprises the steps of: a) contacting the test sample with an antibody or fragment thereof which specifically binds to at least one antigen or peptide derived from PSA for a time and under conditions sufficient to allow for the formation of antigen/antibody complexes; b) adding a labeled free PSA to the resulting test sample-antibody mixture of step (a); and c) determining the amount of PSA in the test sample by assessing the amount of competition between the PSA in the test sample and the labeled free PSA. If free PSA is to be detected, the antibody of step (a) binds specifically to free PSA, and if total PSA is to be detected, the antibody of step (a) binds to total PSA. The peptide or antigen comprises an amino acid sequence of approximately 10–20 residues wherein the sequence is identical to the amino acid sequence of a region of PSA and comprises one or more amino acids nonidentical to the amino acid sequence of hK2. For example, the peptide or antigen is selected from the group consisting of ABT2, ABT4, ABT6, ABT1, ABT7, and ABT16.

Also, the present invention encompasses a kit for determining the presence of PSA in a test sample comprising a container containing an antibody produced in response to immunization by a peptide. The peptide comprises an amino acid sequence of approximately 10–20 residues which is identical to the amino acid sequence of PSA and comprises one or more amino acids nonidentical to the amino acid sequence of hK2. The peptides used to produce the antibodies may be selected from, for example, ABT2, ABT4, ABT6, ATB1, ABT7 and ABT16.

Another kit of the present invention, which may be used for determining the presence of PSA in a test sample, comprises: a) an antibody or fragment thereof which specifically binds to at least one site on PSA; and b) a probe antibody wherein said probe binds to a second site on the PSA. The peptide used to produce the antibody comprises an amino acid sequence of approximately 10–20 residues wherein the sequence is identical to the amino acid sequence of a region of PSA and comprises one or more amino acids nonidentical to the amino acid sequence of hK2. For example, the peptide may be selected from the group consisting of ABT2, ABT4, ABT6, ABT1, ABT7, and ABT16.

The present invention also includes a kit for determining the presence of free PSA in a test sample comprising: a) an antibody or fragment thereof which specifically binds to a peptide comprising an amino acid sequence of approximately 10–20 residues wherein the sequence is identical to the amino acid sequence of a region of PSA and comprises one or more amino acids nonidentical to the amino acid sequence of hK2; and b) labeled free PSA. The peptide used to produce the antibody may be ABT6 or ABT1.

Additionally, the present invention includes a purified peptide derived from PSA comprising an amino acid sequence of approximately 10–20 residues which is identical to the amino acid sequence of a region of PSA and identical to the amino acid sequence of any region of hK2. An example of such a peptide is ABT14 (SEQ. ID. No:14).

BRIEF DESCRIPTION OF THE DRAWINGS

FIG. 6 depicts the titration curves comparing the binding affinity of rabbit anti-ABT4 antiserum to ABT4 peptide, PSA, and hK2a peptide. The affinity rank is ABT4>PSA>hK2a.

DETAILED DESCRIPTION OF THE INVENTION

Figure 1A:
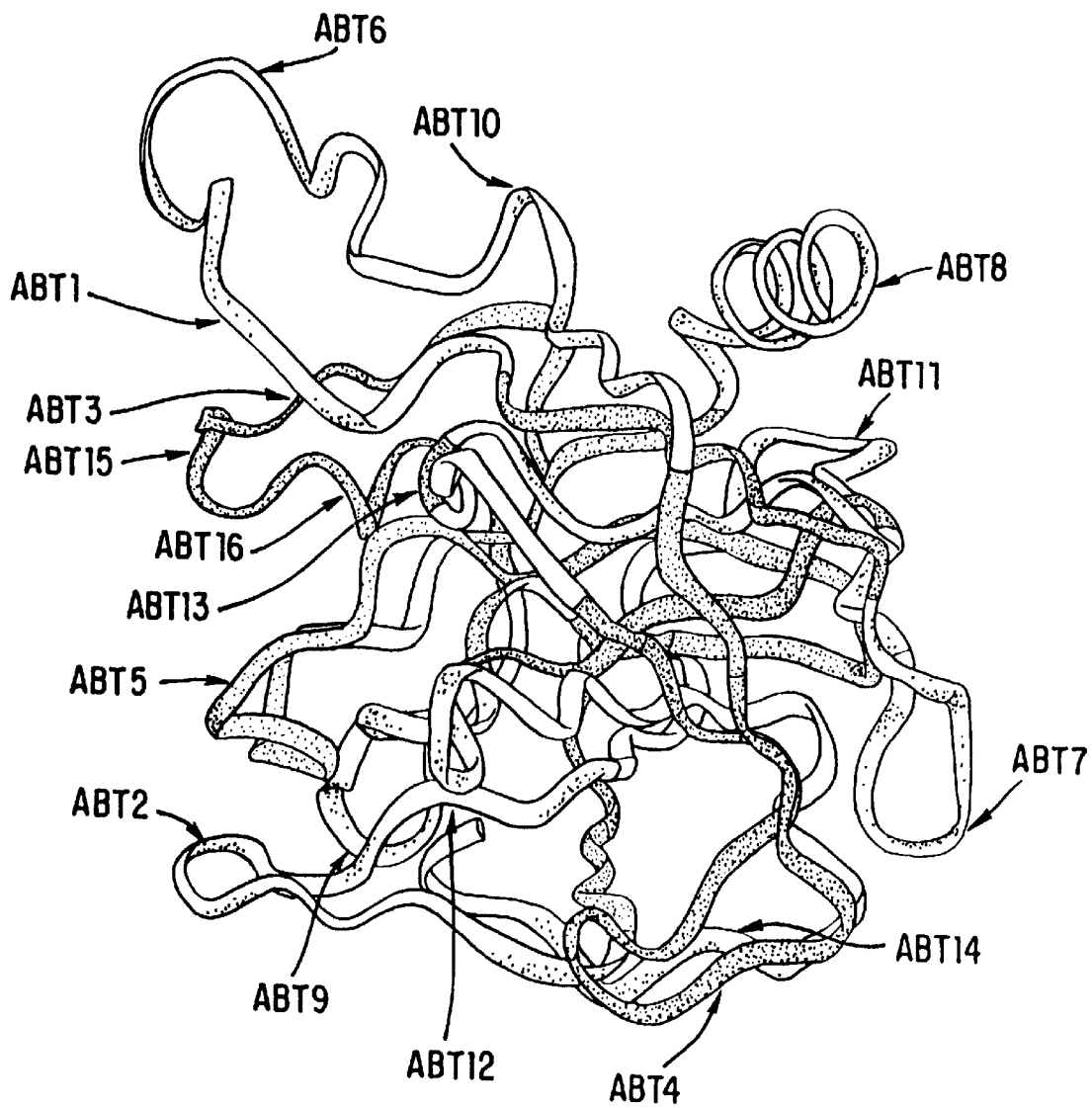
FIG. 1 depicts designed PSA peptides. (A) Locations of the designed peptides on the 3D model of PSA, peptide segments were labeled by the ABT numbering. (B) Sequence and structural alignment of PSA and hK2 (see SEQ. ID. No:17 and SEQ, ID. No:18, respectively). Designed PSA peptide sequences were labeled by the ABT numbering; the nonhomologous or nonidentical residues were indicated in bold in hk2 and shaded in PSA. In addition, two hK2 peptides derived from the hK2 sequence were also labeled as hK2a and hK2b.

The present invention relates to a purified peptide comprising an amino acid sequence or fragment thereof of approximately 10–20 residues which is identical to the amino acid sequence of a region of PSA and comprises one or more amino acids nonidentical to the amino acid sequence of hK2. Alternatively, the amino acid sequence of the peptide may be identical to both the sequence of a region of PSA and a region of hK2. These peptides may be used for different diagnostic and therapeutic purposes. (It should be noted that terminal cysteine groups may be added to "identical" peptides to perform cyclization. "Identical" peptides may also be attached to carrier molecules through the use of cysteine groups.)

The term "identical" is used to describe the degree of relatedness between two polynucleotides or polypeptide sequences. The techniques for determining amino acid sequence "identity" are well-known in the art and include, for example, directly determining the amino acid sequence of the peptide in question, for example, and comparing it to the sequences provide herein. In particular, "identity" refers to an exact match-up of the amino acid sequences of two entities, for example, a peptide of the invention and PSA and/or hK2. "Nonidentical" refers to the lack of an exact match-up of the amino acid sequences in question. The programs available in the Wisconsin Sequence Analysis Package, Version 8 (available from the Genetics Computer Group, Madison, Wis., 53711), for example, the GAP program, are capable of calculating the identity (and similarity) between two polynucleotide or two polypeptide sequences. Other programs for calculating identity between two nucleotide or amino acid sequences are known in the art.

The peptides of the invention were selected by constructing three-dimensional models of PSA and hK2 (Bridon et al., *Urology* 45:801–806 (1995) & Vihinen, M., *Biochem. Biophys. Res. Commun.* 204:1251–1256 (1995)) and then determining which of the exposed regions in the model possessed particular characteristics.

More specifically, a model of PSA was first generated by extrapolating from crystallographic coordinates and amino acid sequences of homologous members of the serine protease family using standard comparative methods.

Subsequently, peptides were selected which appeared to be close to the surface of the molecule based upon direct visualization. Thus, antibodies to such exposed surface peptides are capable of readily binding thereto. Residues which were buried in the protein were not selected.

Additionally, secondary structure was used as a criteria in selecting the peptides disclosed herein. More specifically, peptides were chosen which preferably possessed beta-turns, and protruding loops, as such a structural characteristic has been correlated with production of an immunological response. (See e.g., Krchnak et al., *Methods in Enzymology* 178:586–611 (1989)).

High flexibility and high hydrophilicity were also considered. Such characteristics are associated with immunogenicity and thus the ability to elicit production of antibodies. In particular, the method of Karplus and Shultz was utilized in order to predict high flexibility (see Karplus et al., Naturwissenschaften 72:212–13 (1985)). The method of Hopp and Woods was utilized in order to predict high hydrophilicity (see Hopp et al., *Proc. Natl. Acad. Sci. USA* 78:3824–28 (1981)).

Another factor which was considered in the selection process involves the presence of a naturally occurring disulfide bridge in the peptide and/or the possibility that a beta-coil or turn could be kept in the proper conformation by adding a disulfide bridge within the peptide. Such properties cause the cyclic peptide to more closely mimic the three dimensional configuration of the PSA protein and were therefore useful in the selection process.

After the peptides were selected from the three-dimensional model based upon the above-criteria, the sixteen sequences selected were synthesized in their linear conformations. Several sequences were also produced in their cyclic conformations. Such cyclic forms may act as better immunogens than their linear counterparts.

The designations of the peptides, their amino acid sequences and their molecular weights are illustrated in Table 1 below.

TABLE 1

Synthetic PSA Peptides

| Peptide | Sequence | M.W. verified by MS |
| --- | --- | --- |
| ABT1 (SEQ. ID. No:1) | CNRFLRPGDDSSC | 1468 |
| ABT2 (SEQ. ID. NO:2) | CWGSIEPEEFLTPKKLC | 1980 |
| ABT3 (SEQ. ID. NO:3) | CAQVHPQKVTKFMLC | 1732 |
| ABT4 (SEQ. ID. NO:4) | CLLGRHSLFHPEDTGQC | 1912 |
| ABT5 (SEQ. ID. NO:5) | TSWGSEPCALPERPSLY | 1893 |
| ABT6 (SEQ. ID. NO:6) | CMSLLKNRFLRPGDDSC | 1955 |
| ABT7 (SEQ. ID. NO:7) | SEPAELTDAVKV | 1258 |
| ABT8 (SEQ. ID. NO:8) | HYRKWIKDTIVANA | 1714 |
| ABT9 (SEQ. ID. NO:9) | AGRWTGGKSTCSGDSG | 1527 |
| ABT10 (SEQ. ID. NO:10) | SHSFPHPLYDMSLLK | 1671 |
| ABT11 (SEQ. ID. NO:11) | VMDLPTQEPALGTTC | 1575 |
| ABT12 (SEQ. ID. NO:12) | HSQPWQVLVASRGRAV | 1790 |
| ABT13 (SEQ. ID. NO:13) | PQWVLTAAHCIRNKS | 1724 |
| ABT14 (SEQ. ID. NO:14) | VGGWECEKHSQPWQ | 1670 |
| ABT15 (SEQ. ID. NO:15) | SNDVCAQVHPQKVTKFMLC | 2148 |
| ABT16 (SEQ. ID. NO:16) | DLHVISNDVCAQVHPQK | 1902 |

MS = mass spectroscopy

Although all of the peptides noted above may be used to generate either monoclonal or polyclonal antibodies reactive with PSA, seven of the peptides, namely ABT4, ABT14, ABT6, ABT1, ABT2, ABT16 and ABT7 show specific binding to several known anti-PSA monoclonal antibodies and can therefore be used, for example, as immunogens to elicit epitope-specific polyclonal as well as monoclonal antibodies. An epitope-specific polyclonal antibody is an antibody that is generated with an immunogen representing a small segment of amino acid residues from the parent protein, a protein which has immunogenic properties (i.e., is able to elicit an immune response). The small segment or peptide is considered to be an epitope.

The structure and properties of these seven peptides are as follows:

ABT6 is present in the three-dimensional model of PSA as a protruding loop near the catalytic triad in the active site of PSA (see FIG. 1A). It contains a PSA specific epitope which is blocked by ACT in the PSA-ACT complex, and its amino acid sequence is not identical to hK2. Moreover, it is also immunogenic and therefore has the ability to elicit antibodies (see FIG. 5).

ABT1 is a short version of ABT6. ABT1 contains the same sequence as ABT6 except that five amino acids at the N-terminal (MSLLK) and the serine amino acid at the C-terminal of ABT6 are not included in ABT1 (FIG. 1B). Inhibition studies show that ABT1 inhibits three monoclonal antibodies: 9B10 (40% inhibition), 6:3 (23% inhibition) and 30:5 (50% inhibition). Similar to ABT6, ABT1 contains four amino acids that are not identical to hK2. Therefore, ABT1 should be a PSA specific epitope which is blocked by ACT in the PSA-ACT complex.

ABT4 is present in the three-dimensional model of PSA as a loop and beta-sheet structure distant from the catalytic triad. It is a PSA specific epitope which is not blocked by ACT in the PSA-ACT complex and has an amino acid sequence that is not identical to hK2. It too is immunogenic (see FIG. 6).

ABT14 is present as the N-terminal sequence of PSA. It contains an epitope of PSA and is not blocked by ACT in the PSA-ACT complex. Its amino acid sequence is identical to PSA and hK2 (see FIG. 1B).

ABT16 is present in the three-dimensional model of PSA as an alpha-helical structure. It contains an epitope which is not blocked by ACT in the PSA-ACT complex and may be PSA specific due to its lack of identity with the amino acid sequence of hK2 (see FIG. 1B).

ABT2 is present as a loop structure in the three-dimensional model of PSA. It is an epitope which is not blocked by ACT in the PSA-ACT complex. This epitope may also be PSA specific due to its lack of identity with the amino acid sequence of hK2 (see FIG. 1B).

ABT7 is present in the three-dimensional model of PSA as a loop structure away from the catalytic triad.

It is an epitope which is not blocked by ACT in the PSA-ACT complex, and may be PSA specific due to its lack of identity with the amino acid sequence of hK2 (see FIG. 1B).

In particular, the peptides of the present invention which are reactive with antibodies specific for free PSA (i.e., "free PSA-associated epitopes") can be used to generate antibodies (i.e., "free, specific antibodies") in polyclonal and monoclonal systems by injection with peptide-carrier proteins or in other immunogenic forms. Examples of such free PSA-associated epitope are ABT6 and ABT1. Suitable peptide carrier proteins include, for example, those proteins which have a sufficient molecular weight such that they are immunogenic. Examples include but are not limited to bovine serum albumin, keyhole limpet hemocyanin, ovalbumin and synthetic carriers such as poly-L-lysine or poly-L-glutamine which allow for multiple attachments of the peptide. (For a general discussion of generating antisera by linking peptides to carriers, see Methods in Molecular Biology, ed. J. Walker, Vol. 32, pp. 389–400 (1994).)

Additionally, the peptides of the invention which are reactive with antibodies specific for total PSA (i.e., "total PSA-associated epitopes") may be used to generate "total PSA antibodies" in polyclonal and monoclonal systems by injection with peptide-carrier proteins or in other immunogenic forms. Examples of such total PSA-associated epitopes include ABT4, ABT14 and ABT16.

It should be noted that "free associated" antibodies or epitopes are those antibodies and the epitopes associated with them that demonstrate partial or essentially total specificity for free PSA as compared to PSA-inhibitor complexes, the most common of these being PSA-alpha-1-antichymotrypsin (PSA-ACT) and PSA-alpha-2-macroglobulin (PSA-A2M).

Additionally, "total" PSA antibodies or epitopes are those antibodies and the epitopes associated with them that demonstrate the ability to bind to both PSA and PSA-ACT complexes in a significantly equivalent manner.

The advantage of being able to measure the level of free and total PSA is quite signficant. As noted above, the ratio of free PSA to total PSA is lower in patients with prostate cancer than in patients with BPH. Thus, the addition of a free to total PSA ratio value to the results of a digital rectal examination can aide in the early detection of prostate cancer and thus reduce the number of biopsies required (McCormack et al., *Urology* 45:729–44 (1955), Partin et al., *J. Urol.* 152:1358–68 (1994), Lilja et al., *Clin. Chem.* 37:1618 (1991), Christinesson et al., *J. Urol.* 150:100–105 (1993)).

The present invention also encompasses kits containing antibodies produced in response to, or directed against, the peptides of the invention. Such antibodies may be elicited, for example, in response to immunization with one or more of the peptides.

It should be noted that "total PSA" is used to describe the ability of an immunoassay to recognize immunologically detectable forms of PSA, especially free PSA and PSA-ACT complexes, the two most common PSA forms in serum. Since the percentage of free PSA and PSA-ACT varies from man to man, total PSA assays are necessary to detect both forms (McCormack et al., *Urology* 45:729–44 (1995) and Partin et al., *J. Urol.* 152:1358–68 (1994)).

Also, those free PSA-associated and total PSA-associated peptides of the invention which are not identical with hK2 can be used to generate PSA-specific, non-hK2 cross-reactive antibodies to free PSA or total PSA in polyclonal and monoclonal systems by injection with peptide-carrier proteins or in other immunogenic forms. (Since there is a high degree of amino acid and structural identity between PSA and hK2, it is difficult to produce antibodies which are not cross-reactive.)

Additionally, free PSA-specific immunoassays can be configured using a combination of free specific antibodies and total PSA antibodies referred to above. (Currently available total PSA antibodies can be substituted for the total PSA antibodies of the present invention.)

In particular, a sandwich assay can be utilized with one free specific antibody and one total PSA antibody generated using the appropriate peptides of the invention. A typical two-step sandwich assay for PSA consists of a first antibody to PSA immobilized on a carrier (e.g., a microtiter plate, a polystyrene bead, and a latex microparticle) to which the specimen, controls or calibrators containing PSA are added. The PSA in these samples binds to the carrier bound PSA antibody during an incubation phase. The unbound material is removed by washing, for example, with buffer. A probe antibody to PSA is then added and binds to a second site on the PSA during an incubation phase. The excess probe antibody is removed by washing with buffer. The probe antibody may be labelled with a radioactive isotope, such as $I^{125}$, or with an enzyme, for example, horseradish peroxidase, alkaline phosphatase or glucose oxidase. The amount of probe bound by the PSA can be determined by determining the level of radioactivity or by adding an enzyme substrate and detecting the product formed. The amount of PSA is then determined from a calibration curve using standards with known PSA levels.

It should also be noted that the invention includes a kit which can be used to carry out the above-described sandwich assay. Such a kit may include, for example, an antibody or fragment thereof which specifically binds to at least one site on PSA and a probe antibody which binds to a second site on PSA. The antibodies are generated using the peptides of the invention.

A one-step assay combines the capture antibody, probe antibody, and PSA containing samples in one incubation step followed by a wash step and a read step. For a free PSA specific assay, either the probe or carrier antibody must be free specific (Chan et al., *Clin. Chem.* 33:1916–1920 (1987), Ambruster, *Clin. Chem.* 39:181–195 (1993), Lilja et al., *Clin. Chem.* 37:1618 (1991) and Christenesson et al., *J. Urol.* 158:100–105 (1993)).

Furthermore, the peptides of the present invention may be used to generate antibodies for a competitive assay for free PSA. More specifically, the assay involves the use of one free specific antibody and labelled free PSA. (Labelled free peptide can replace labelled free PSA if more convenient.)

In a competitive assay for free PSA, the sample, controls or calibrators are incubated with an antibody to free PSA. Following this step or simultaneously with this step, radiolabeled purified free PSA is added. (In addition to the use of a radioactive label, the PSA may also be labeled with other reporter molecules such as enzymes or chemicals which generate chemiluminescence or fluorescence (see e.g., Chan et al., Clin. Chem. 33:1916–20 (1987)). A second antibody to the free PSA antibody, for instance, goat anti-mouse IgG, if the free PSA antibody is a mouse monoclonal, is added to precipitate the free PSA antibody and any PSA that is bound. Alternatively, the second antibody can be attached to a solid phase, such as, for example, a latex microparticle or polystyrene bead. The mixture is washed with buffer, and the amount of radioactivity determined. The amount of PSA in the sample is determined by comparing the amount of competition of the PSA in the sample for the binding of the labeled PSA. The concentration of PSA is determined using a calibration curve consisting of standards with known levels of PSA (Chan et al., Clin. Chem. 33:1916–1920 (1987)).

The invention includes a kit which utilizes the competitive assay components described above. More specifically, such a kit may include an antibody or fragment thereof which binds to at least one of the peptides of the invention. The kit would also include, for example, labelled free PSA.

Also, a total PSA specific immunoassay can be generated using a combination of two total PSA-associated antibodies, raised against the peptides of the present invention, one or both of which may be non-hK2 cross-reactive antibodies. Alternatively, one of the above-listed antibodies may be used in combination with a currently available total PSA antibody. (The use of a non-hK2 cross-reactive antibody generates a PSA, non-hK2 cross-reactive assay.) The total PSA specific assay is performed as described above for a free PSA sandwich assay except both antibodies must be reactive with total PSA. If both of the antibodies are reactive with total PSA and with hK2, the assay that is generated will detect both PSA and hK2. If either the probe or capture antibody is specific for PSA (non-hK2 reactive), the assay will only detect total PSA. The advantage of the first format is that both kallekriens produced by the prostate (i.e., PSA and hK2) are detected. The advantage of the second format is that the assay will be specific for the PSA molecule only.

Additionally, a competitive assay for total PSA can be generated using one of the total PSA antibodies raised against a peptide of the invention, or one of the PSA specific, non-hK2 cross-reactive antibodies raised against a peptide of the invention, and labelled free or complexed PSA. Labeled free peptide can replace labelled free PSA in the assay. (Again, the use of a non-hK2 cross-reactive antibody generates a PSA, non-hK2 cross-reactive assay.) The steps of the assay are the same as for the competitive free PSA assay, except that a total PSA antibody or a total PSA, non-hK2 reactive antibody is used instead of an antibody to free PSA.

Furthermore, an immunoassay for the PSA-ACT complex can be generated using a total PSA antibody (which may possibly be a non-hK2 cross-reactive antibody) to form a sandwich with currently available antibodies to ACT. As noted above, the PSA-ACT complex is the major form of PSA in the serum. An assay for PSA-ACT is more specific than a total PSA assay in that one "type" of molecule is being detected. Thus, using assays for free PSA and PSA-ACT, it is possible to detect the two major forms of PSA independently.

The use of ratios of PSA-ACT to total PSA has been shown to improve the specificity of PSA in the early detection of prostate cancer since patients with prostate cancer have higher levels of PSA-ACT than do patients with BPH (Stenman et al., Cancer Res. 51:222–26 (1991) and Stenman et al., Lancet 334:1594–1598 (1994)).

Additionally, it should be noted that the PSA peptides of the present invention can be used either alone or attached to a carrier such as a protein (for example, bovine serum albumin, keyhole limpet hemocyanin or ovalbumin) or to a chemical backbone (for example, poly-L-lysine or poly-L-glutamine). In a competitive assay, the peptide or peptide carrier can be used in place of PSA to inhibit the anti-PSA peptide antibody as a control (or as a calibrator) for the assay. For a sandwich assay, two peptides bound to a common carrier backbone can be used to generate a bivalent molecule containing two peptides (bivalent peptide control or calibrator) that can sandwich in an assay using antibodies to these two peptides. During the use of these artificial controls, the bivalent peptide control is included as a sample, and its level is monitored for assay validity. Furthermore, with respect to the use of the bivalent peptides as calibrators, various concentrations of the bivalent peptides may be used to generate a calibration curve for the assay. Potential advantages are stability, cost of manufacture and the use of a very defined control or calibrator.

Furthermore, peptides having sequences of regions of hK2 can be used to generate hK2 specific antibodies in polyclonal and monoclonal systems by injection with peptide-carrier proteins or in other immunogenic forms. Additionally, immunoassays specific for hK2 may be configured using a combination of these hK2 specific antibodies or one of these antibodies in combination with a total PSA antibody if it is hK2 cross-reactive.

More specifically, a sandwich assay format using one or two hK2 specific antibodies or one hK2 specific antibody assay could be generated with one hK2 specific antibody and labelled hK2 or hK2 peptide (see WO 95/03334).

Thus, all of the above assays can be carried out with hK2 peptides which correspond to the regions of the PSA molecule from which the peptides of the invention were selected.

Additionally, it should be noted that the hK2 peptides, referred to above, can be used singly or in combination alone or attached to a protein, such as bovine serum albumin, keyhole limpet hemocyanin, or ovalbumin, or to a chemical backbone, such as poly-L-lysine or poly-L-glutamine. In a competitive assay, the peptide or peptide carrier could be used to inhibit the anti-hK2 peptide antibody as a control (or as a calibrator) for the assay. For a sandwich assay to hK2, two hK2 peptides bound to a common carrier backbone could be used to generate a bivalent peptide control or calibrator that could sandwich in an assay using antibodies to these two peptides. During this use as an artificial control, the bivalent peptide control is included as a sample and its level monitored for assay validity. With respect to the use of the bivalent peptides as calibrators, various concentrations of the bivalent peptides may be used to generate a calibration curve for the assay. Potential advantages are stability, cost of manufacture and the use of a very defined control or calibrator.

It should also be noted that polyclonal antibodies produced against PSA contain antibodies reactive with both free and total PSA. The free specific antibodies in the polyclonal anti-PSA antibody can be bound to a column containing the free specific peptides of the current invention (e.g., ABT6 or ABT1) attached to a solid phase, such as, for example, Cyanogen Bromide Activated Sepharose CL4B. (For a general discussion of the purification of antisera on peptide columns, see Methods in Molecular Biology, ed. M. Manson, Vol. 10, pp. 39–41 (1992).) The non-free peptide specific antibody is washed through the column with buffer. The free specific antibodies are then eluted with high or low pH or chaotropic agents to yield free specific polyclonal antibodies which can be used in assays for free PSA.

Alternatively, epitope specific antibodies to total PSA can be purified from polyclonal antisera. For example, peptides ABT4, ABT14, or ABT16 can be bound to a solid phase carrier and used to produce a column. The polyclonal antibodies reactive with the peptide bind to the peptide on the column, while non-reactive peptides are washed through the column with buffer. The bound polyclonal antibodies are then eluted with high or low pH or chaotropic agents to yield peptide epitope specific polyclonal antibodies. These antibodies can be used in immunoassays to generate assays that can react equally to both free PSA and PSA-ACT, in contrast to current sandwich assays polyclonal assays that have a bias towards free PSA (see copending U.S. patent application Ser. No. 08/174,964). Since the proportion of free PSA and PSA-ACT varies from person to person, there is a theoretical advantage of measuring free PSA and PSA-ACT equally (McCormack et al., Urology 45:729–44 (1995), Stamey et al., Cancer 74:1662–66 (1994) and Stamey, Urology 45:173–84 (1995)).

It should also be noted that the anti-PSA antibodies created using the peptides of the present invention can be used to detect PSA in frozen or paraffin sections of normal, benign or cancerous tissues or cell lines by way of immunohistochemical methods. For example, the labeled antisera may be added to the sample of interest, followed by an incubation and wash step. (Examples of suitable labels include, but are not limited to, an enzyme such as alkaline phosphatase, glucose oxidase or peroxidase, a radiolabel such as $I^{125}$, or a fluorochrome such as fluoroscein isothiocyanate.) Presence of PSA is then assessed by detection of absorbance from chromophore for the enzyme-labelled antibody, detection of radiodecay for the radiolabeled antibody, or detection of fluorescence for the fluorochrome labeled antibody. Other labels and detection methods may also be used.

Additionally, since the peptides of the present invention elicit antibodies, the peptides may also be used in mammalian vaccines.

The present invention can be illustrated by the use of the following nonlimiting examples:

EXAMPLE I

DESIGN, SYNTHESIS, AND EPITOPE MAPPING OF THE PEPTIDES

A. Peptide Design Strategy:

The potential peptide epitopes were designed based on a molecular model of PSA and amino acid sequence alignment (Bridon et al., Urology 45:801 (1995) & Vihinen, M., Biochem. Biophys. Res. Commun. 204:1251–1256 (1994)). The locations of sixteen peptides designed from the three dimensional model of PSA are shown in FIG. 1A. The original protein sequence alignment of PSA and hK2 was obtained by Pileup from the Wisconsin Sequence Analysis Package (Genetic Computer Group, University Research Park, 575 Science Drive, Suite B, Madison, Wis.). These alignments were then further edited according to the more accurate method of comparative modeling as described by Greer (J. Greer, Proteins 7:317 (1990)). The final protein sequence alignment of hK2 and PSA is shown in FIG. 1B.

As noted above, sixteen PSA peptides were generated based on the primary amino acid sequence of PSA and the location of these peptides in the 3D model.

Generally, these peptide sequences were surface accessible on the PSA molecule and showed certain secondary structural features, such as a protruding loop, an alpha-helix or a beta-turn. In addition, most of the designed peptides (i.e., $^{15}/_{16}$) contained one or more amino acid residues that were different from human Kallikrein-1 (hK2).

B. Peptide Synthesis:

Designed peptides were synthesized by the stepwise solid-phase method of Merrifield (Merrifield, R. B., J. Am. Chem. Soc. 85:2149–2154 (1963)) on Applied Biosystem 431A Synthesizer (Foster City, Calif.) using standard Fmoc (9-fluorenylmethoxycarbonyl) chemistry. Peptides were cleaved and deprotected with a mixture of 82% TFA, 5% phenol, 5% H2O, 5% thioanisole and 2.5% ethanedithiol for 2–4 hours at 25° C. and precipitated by addition of cold ether. Crude peptides were purified by reverse phase HPLC using a 5–50% acetonitrile gradient containing 0.1% TFA. The homogeneity and identity of the purified peptides were confirmed by electro-spray mass spectrometry analysis. All peptides were determined to be at least 95% pure. In order to cyclize the peptides, peptides were generated which had one cysteine residue added to the carboxyl and amino terminals. Cyclic peptides formed by an intramolecular disulfide bridge were synthesized using the air oxidation method previously described (Tam et al., Proc. Natl. Acad. Sci. USA 83:8082–8086 (1986)). Briefly, purified linear peptides were dissolved in 0.1 mM Tris-HCl buffer (pH 8.4) at a concentration of 0.5 mg/ml and stirred at 25° C. for varying periods of time while exposed to air. HPLC was used to monitor the completion of oxidation. Cyclic peptides were purified as described above, and the formation of intramolecular disulfide bonds was confirmed by electro-spray mass spectra.

C. Epitope Mapping:

I. Indirect ELISA

An indirect ELISA assay was used to determine the reactivity and specificity of anti-PSA mAbs and pAbs. For the assay, 96 well microtiter plates (Costar, Cambridge, MA) were coated with PSA (0.5 micrograms/well, Abbott Laboratories, in house product, code# 91969, purified from seminal fluid) or peptides (0.1 mg/well) in 0.1 M carbonate-bicarbonate buffer (pH 9.0) overnight at 4° C. The plates were blocked with 1% BSA in PBS buffer (0.008 M sodium phosphate, 0.002M potassium phosphate, 0.14 M sodium chloride and 0.01M potassium chloride, pH 7.4) for 1 hour, then anti-PSA mAbs or pAbs (100 microliters/well) at varying dilutions were added. After incubation for 1 hour at 25° C., the wells were washed with PBS buffer containing 0.5% Tween 20, then 100 microliters/well of alkaline phosphatase-conjugated antibody (goat anti-mouse IgG or goat anti-rabbit IgG—from Pierce, Rockford, IL) at 5000 fold dilution was added and incubation continued for 1–2 hr at 25° C. After washing, 100 microliters/well of p-nitrophenyl phosphate substrate (Pierce, Rockford, Ill.) was added and the absorbance was measured at 405 nm using an automated microtiter plate reader (Molecular Devices Corp. Menlo Oaks, Calif.).

II. Competitive Immunoassays (A). Two-site combinations of capture antibody and Europium chelate (Eu)-labeled antibody was used to determine the inhibition of mAbs binding to PSA by the synthetic peptides derived from PSA. Briefly, free PSA (0.05 pmol/well, Wallac, O Y, Turku, Finland) in 0.100 mL of Delfia® buffer (Wallac, O Y) (i.e., a blocking buffer containing 50 mM Tris-HCl (pH 7.75), 0.9% NaCl, 0.05% Na-azide, 0.01% Tween 40, 0.05% bovine-gammaglobulin, 20 µM DTPA, 0.5% BSA, 10 µg/mL native mouse IgG, 5 µg/mL denatured mouse IgG and 20 µg/mL cherry red) was added to microtiter wells coated with the various anti-PSA antibodies being used for capture (1–2 µg/well of antibody) and incubated for 1 hour at 25° C. (Free or total antibodies may be used.) After washing with Delfia® wash solution, peptides (62,500–1,000,000 molar excess to PSA) in 25 mL Delfia® buffer were added together with the Europium chelate-labeled anti-PSA antibody (0.05 pmol), and incubation was continued for 1 hour at 25°0 C. After another four washings, the amount of bound Eu-labeled antibody was determined with time-resolved fluorometry previously described (Pettersson et al., *Clin. Chem.* 41:1480–88 (1995) & Hemmilia et al., *Anal. Biochem.* 137:335–43 (1984)).

(B). Two-site combinations of capture antibody and alkaline phosphatase-conjugated antibody were also used to determine the inhibition of mAbs binding to PSA by the synthetic peptides, using alkaline-phosphatase labelled antibodies. Combinations of probe and capture antibodies, which included antibodies with specificities for either free or total PSA, were chosen so that these combinations could bind to form a sandwich. As described above, various anti-PSA capture mAbs (i.e., either free or total) (0.4 pmol/well) in 100 ml PBS buffer (pH 7.4) were added to coated microtiter wells (1 µg/well) and incubated for 1 hour at 25° C. After washing with PBS buffer containing 0.5% Tween 20, peptides were added (50,000–500,000 molar excess to PSA) in 50 µl PBS buffer together with alkaline phosphatase-conjugated antibody(20 ng/well, Abbott Laboratories) and incubated for 1–2 hr at 25° C. After another four washings, 100 µl/well of p-nitrophenyl phosphate substrate (Pierce Chemical Co., Rockford, Ill.) was added and the absorbance was measured at 405 nm using an automated microtiter plate reader.

D. Results:

I. Epitopes of mAbs preferentially binding to free PSA:

All sixteen synthetic peptides (Table 1) were screened with a series of monoclonal anti-PSA antibodies using a competitive immunoassay described in section C-II-A. ABT6 peptide showed specific binding to mAb 9B10 and 5A10 that are specific for free PSA (Lilja et al., *Clin. Chem.* 37:1618–25 (1991), Pettersson et al., *Clin. Chem.* 41:1480–88 (1995) & Lovgren et al., *Biochem. Biophys. Res. Commun.* 213:888–95 (1995)). ABT6 peptide also selectively bound to mAb 2E9 (Lovgren et al., *Biochem. Biophys. Res. Commun.* 213:888–95 (1995)) and H68 (obtained by Abbott Labs.) which binds a region close to that covered by ACT in the PSA-ACT complex.

Figure 2A:
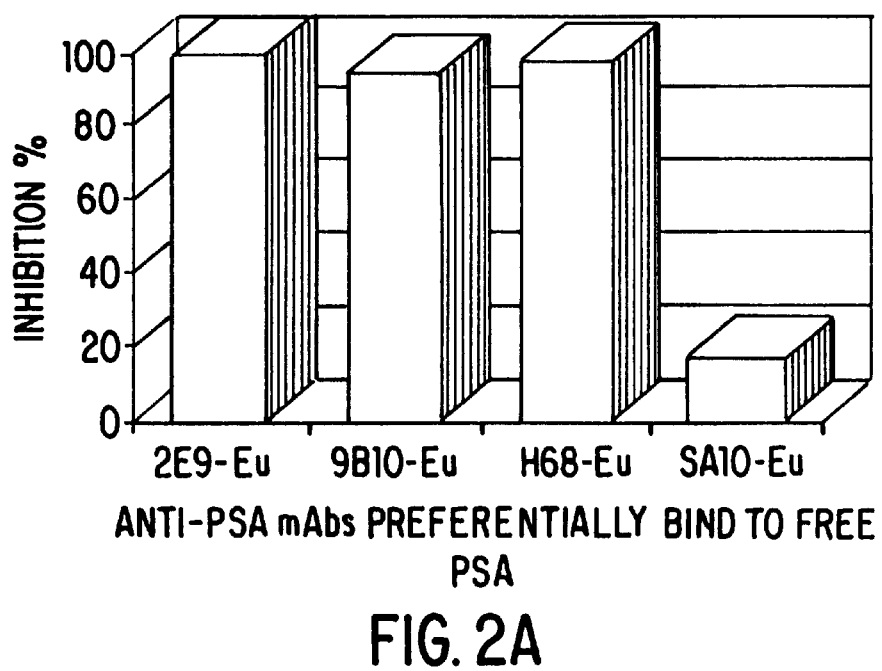
FIG. 2 depicts (A) the inhibition of free PSA specific monoclonal antibodies and of monoclonal antibodies which preferentially detect free PSA and (B) the titration curves showing the binding specificity of mAb 2E9, an antibody which preferentially detects free PSA to ABT6 peptide and PSA, but not to the hK2b peptide.

The percent inhibition of the mAbs binding to PSA by the ABT6 peptide is shown in FIG. 2A. These data demonstrate that ABT6 contain an epitope on PSA recognized by the mAbs specific for free PSA or that show preferential binding to free PSA.

Figure 2B:
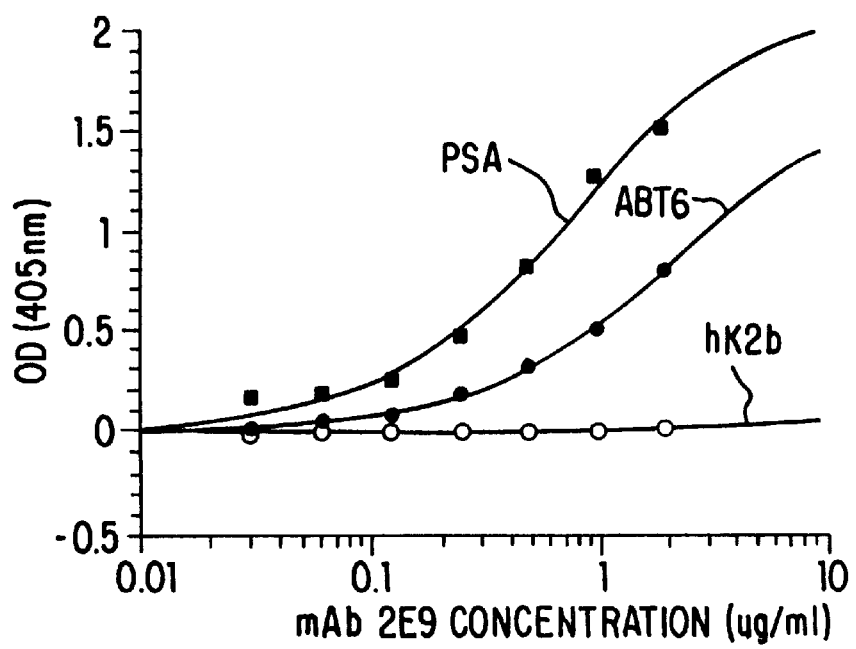

As shown in FIG. 1B, ABT6 peptide contains several amino acids which are different from the hK2 sequence. To demonstrate that the ABT6 peptide represents a PSA specific epitope, the corresponding hK2b peptide (see FIG. 1B) was synthesized. The specific binding of ABT6 peptide, hK2 peptides and PSA to mAb 2E9 were compared using indirect ELISA as described in section C-I. FIG. 2B shows the ELISA results. It is clear that 2E9 shows specific binding to both PSA and ABT6 peptide, but not to hK2 peptide. Based on these data, it is concluded that ABT6 peptide, which is a protruding loop on the 3D model of PSA, represents a PSA specific epitope that will be blocked or sterically hindered by the binding of ACT to PSA in the PSA-ACT complex. In addition, this epitope has some specificity to PSA, based on comparisons between ABT6 and hk2b.

Figure 3A:
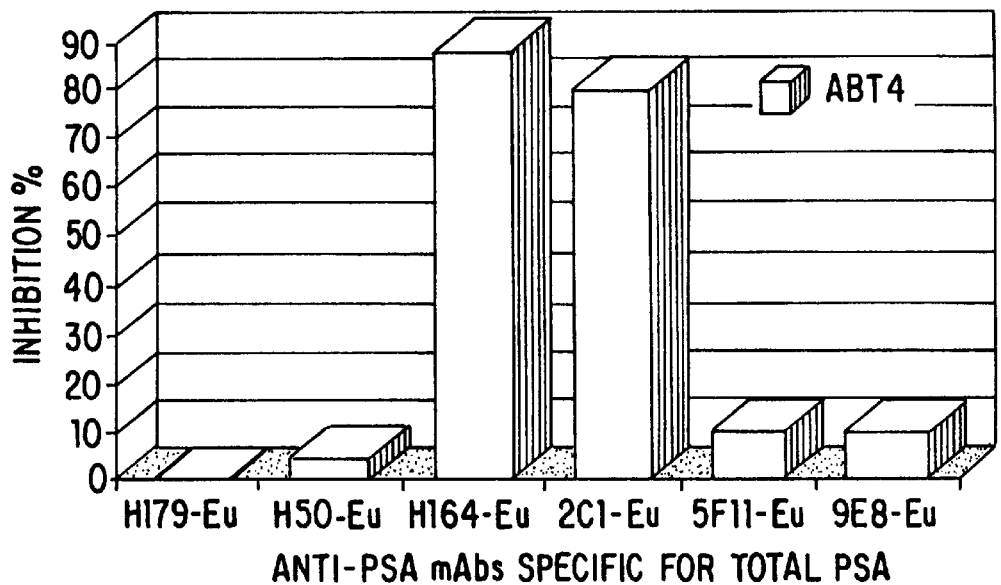
FIG. 3 depicts (A) the inhibition of total PSA specific mAbs binding to PSA by ABT4 peptide, (B) the inhibition of total PSA specific mAbs binding to PSA by ABT14 and ABT16 peptides and (C) the titration curves showing the binding specificity of mAb H164 to ABT4 peptide and PSA, but not to the hK2a peptide.
Figure 3B:
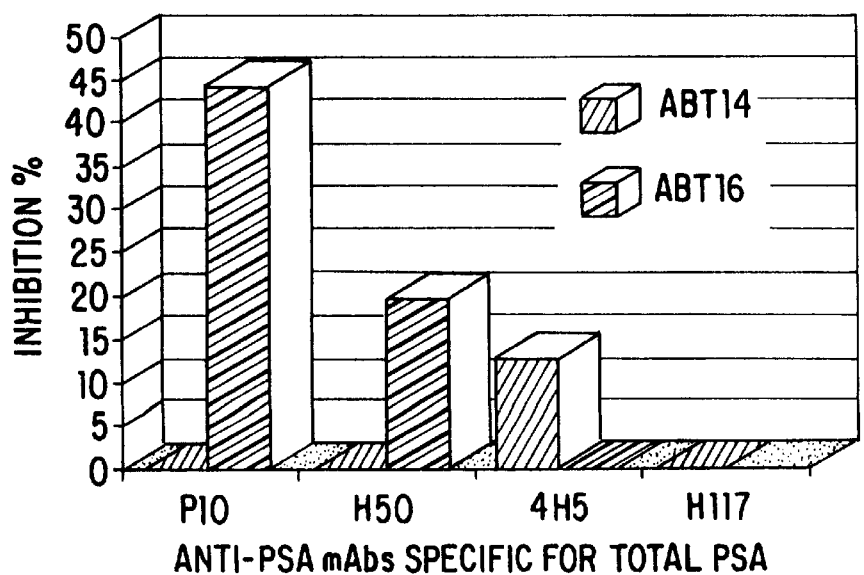

II. Epitopes of mAbs specific for total PSA:

Three synthetic peptides, ABT4, ABT14 and ABT16 were identified to contain epitopes of several mAbs that were specific for total PSA in the competitive immunoassays described in section C-II-A and B. ABT4 peptide inhibits 80 to 90% PSA binding to mAb 2C1 (Lovgren et al., *Biochem. Biophys. Res. Commun.* 204:1251–56 (1994)) and H164 (produced by standard hybridoma techniques at Abbott Labs., Abbott Park, Illinois), respectively (FIG. 3A). ABT14 selectively inhibits PSA binding to mAb 4H5 (Lovgren et al., *Biochem. Biophys. Res. Commun.* 204:1251–56 (1994)), and ABT16 inhibits PSA binding to mAb P10 (CanAg Diagnostics Inc., Gothenberg, Sweden), and H50 (produced by standard hybridoma techniques at Abbott Labs., Abbott Park, Ill.) (FIG. 3B). However, the percent inhibition of both peptides was relatively weak compared to ABT4 peptide. Thus, ABT14 and ABT16 may represent partial epitopes of mAb 4H5, P10 and H50.

Figure 3C:
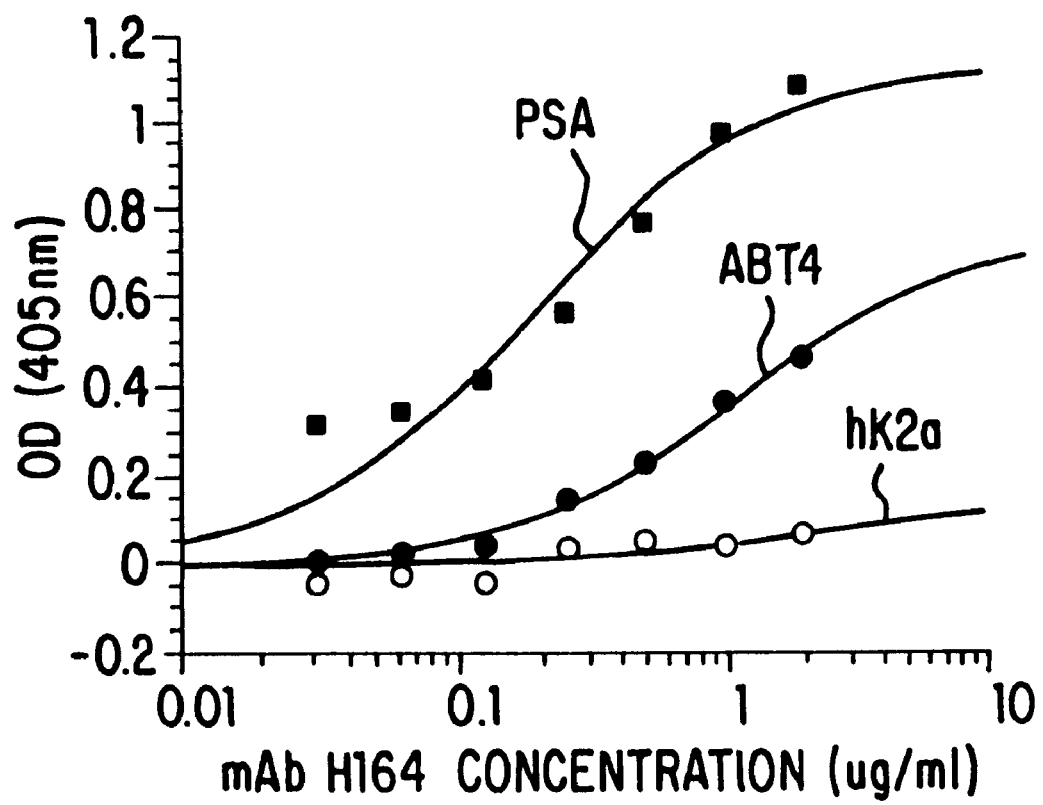

From the sequence alignment (FIG. 1B), the potent ABT4 peptide contained several amino acids that were different from the hK2 sequence. To evaluate the epitope specificity of the ABT4, the corresponding hK2a peptide was synthesized. The specific binding of ABT4, hK2a peptides (see FIG. 1B) and PSA to mAb H164 was determined using indirect ELISA as described in section C-I, and the results are shown in FIG. 3C. These data (FIG. 3C) demonstrated that MAb H164 bound specifically to PSA and PSA peptide ABT4, but not to the hK2a peptide. Therefore, ABT4, which exhibited a loop and beta-strand structure on the 3D model of PSA, represented a PSA specific epitope and this epitope will not be blocked by ACT in the PSA-ACT complex.

Figure 4:
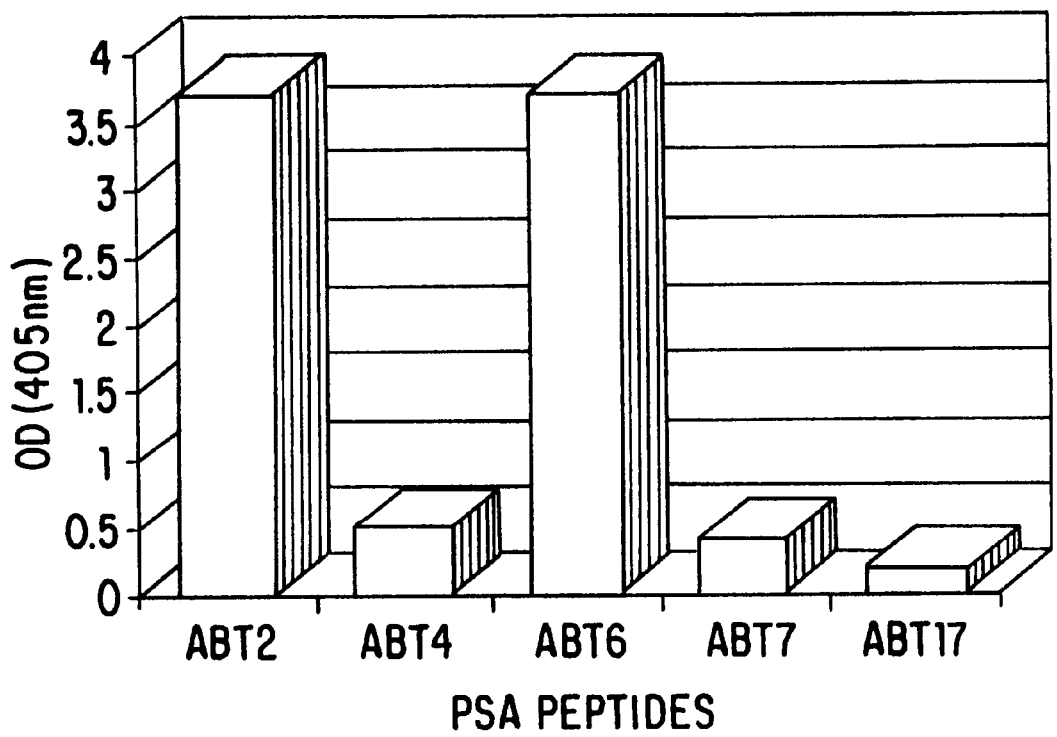
FIG. 4 depicts the specific binding of the alkaline phosphatase-labeled goat anti-PSA antiserum to the synthetic PSA peptides.

III. Anti-PSA pAb reactivity against synthetic peptides:

Synthetic peptides were also screened by a direct ELISA assay format which utilized a goat anti-PSA antiserum conjugated to alkaline phosphatase. In particular, peptides were coated on microtiter plates and detected by enzyme-labelled anti-PSA polyclonal antibodies. The goat anti-PSA antiserum was produced by immunization with free PSA. As a polyclonal antisera, this goat anti-PSA can be expected to exhibit antibodies to multiple free and total PSA associated epitopes. The ELISA results are shown in FIG. 4. In addition to those epitopes identified by mAbs as described above, two new epitopes, ABT2 and ABT7, were identified by the anti-PSA antiserum.

EXAMPLE II

IMMUNOGENICITY OF ABT6 PEPTIDE (Free PSA epitope)

A. Immunization with ABT6 peptide

Antiserum was elicited by immunizing rabbits with PSA peptide ABT6 coupled to the carrier protein KLH (keyhole limpet hemocyanin) at Bio-Synthesis, Inc. (Lewisville, Tex.) using standard commercially available techniques.

B. Reactivity and specificity of anti-ABT6 antiserum

Figure 5:
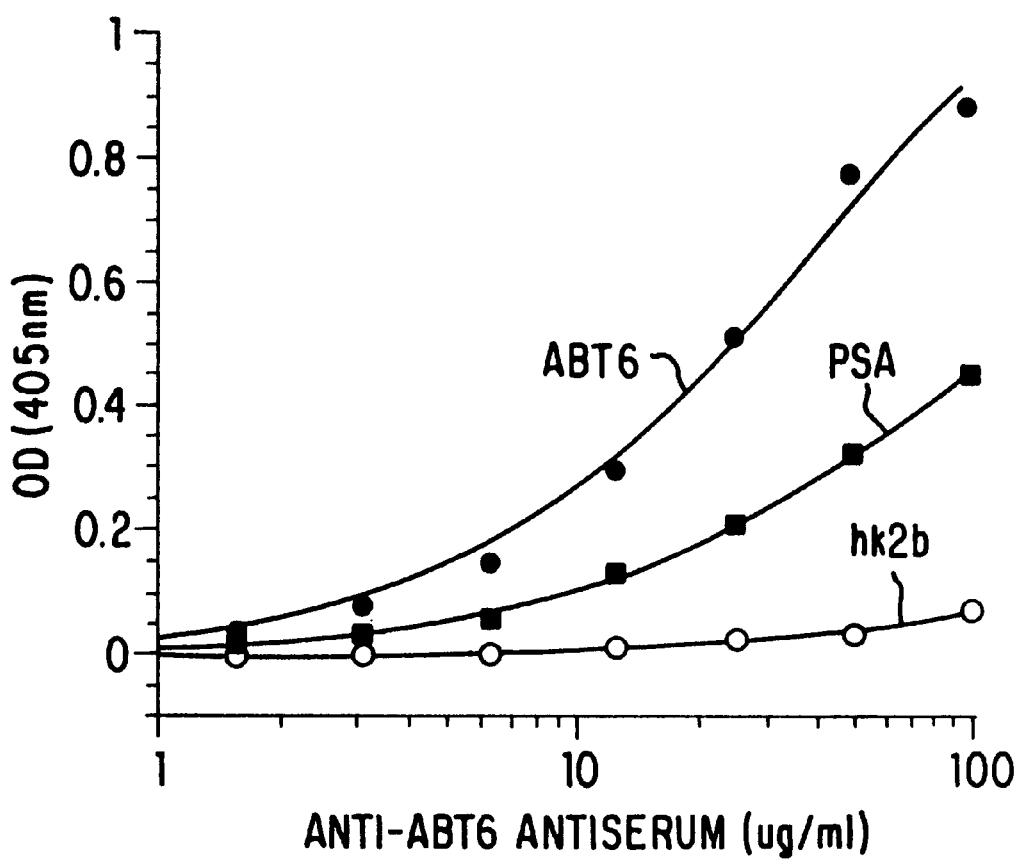
FIG. 5 depicts the titration curves showing the binding specificity of rabbit anti-ABT6 antiserum to both ABT6 peptide and PSA, but not to hK2b peptide.

The reactivity and specificity of antiserum anti-ABT6 was evaluated by estimating the relative binding affinities (Wang et al., *Urology* 39:1–5 (1982)) for PSA, PSA peptide ABT6 and hK2 peptide hK2b as described in Example I. The indirect ELISA format described in Section C-I of Example 1 was used for these studies and the data are shown in FIG. 5. These data demonstrated that the anti-ABT6 antiserum specifically bound only to ABT6 peptide and PSA with high affinity. There is almost no binding for the hK2b peptide.

EXAMPLE III

IMMUNOGENICITY OF ABT4 PEPTIDE (Total PSA epitope)

A. Immunization with ABT4 peptide

Anti-ABT4 antiserum was elicited by immunizing two rabbits with PSA peptide ABT4 coupled to the carrier protein KLH at Bio-Synthesis, Inc.(Lewisville, Tex.).

B. Reactivity and specificity of anti-ABT4 antiserum

Figure 6:
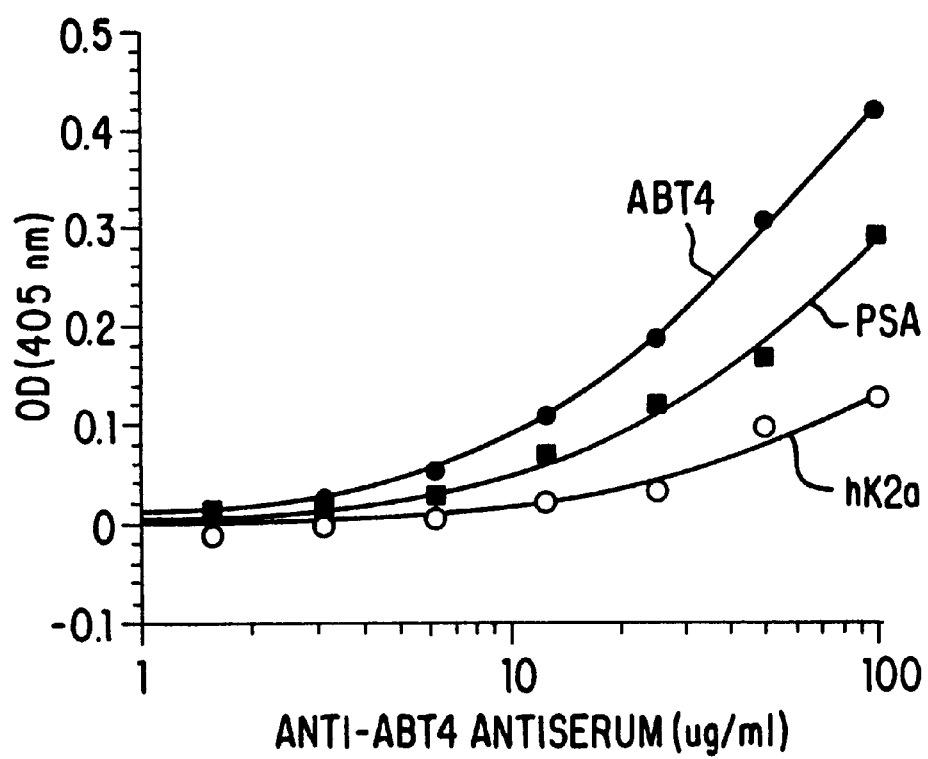

The reactivity and specificity of Anti-ABT4 antiserum were evaluated by estimating the relative binding affinities (Wang et al., Oncology 39:1–5 (1982)) for PSA, PSA peptide ABT4 and hK2 peptide (hK2a) as described in Example I. The indirect ELISA assay format described in Section C-I of Example I was used for these studies and the data are shown in FIG. 6. These data demonstrated that although the anti-ABT4 antiserum binds to both ABT4 peptide and PSA, there is some cross reactivity with the hK2A peptide. The relative affinity was ABT4 >PSA >hK2a.

We claim:

1. An antibody specific for free PSA produced in response to immunization by a peptide selected from the group consisting of ABT6 and ABT1.

2. The antibody of claim 1 wherein said antibody is monoclonal.

3. The antibody of claim 1 wherein said antibody is polyclonal.

4. An antibody specific for total PSA produced in response to immunization by a peptide selected from the group consisting of ABT14 and ABT16.

5. The antibody of claim 4 wherein said antibody is monoclonal.

6. The antibody of claim 4 wherein said antibody is polyclonal.

7. A method for detecting PSA in a test sample suspected of containing PSA comprising the steps of:
   a) contacting the test sample with an antibody or fragment thereof which specifically binds to at least one site on a peptide or antigen for a time and under conditions sufficient to allow for the formation of antigen/antibody complexes
   wherein said peptide or antigen is selected from the group consisting of ABT2, ABT6, ABT1, ABT7, and ABT16 and said antibody or fragment thereof has been produced in response to said peptide or antigen;

b) adding a probe antibody to said resulting antigen/antibody complexes for a time and under conditions sufficient to allow said probe to bind to said bound antigen, wherein said probe binds to a second site on said peptide or antigen; and c) determining the amount of bound probe and thus the amount of PSA in said test sample.

8. The method of claim 7 wherein said antibody of step (a) is attached to a solid phase.

9. The method of claim 7 wherein said antibody of step (b) is labelled with a radioactive isotope.

10. The method of claim 7 wherein one antibody is specific for free PSA and the other antibody is specific for total PSA, or both antibodies are specific for total PSA.

11. A method of detecting PSA in a test sample suspected of containing PSA comprising the steps of:

a) contacting the test sample with an antibody or fragment thereof which specifically binds to at least one peptide or antigen derived from PSA for a time and under conditions sufficient to allow for formation of antigen/antibody complexes
wherein said peptide or antigen is selected from the group consisting of ABT2, ABT6, ABT1, ABT7 and ABT16 and said antibody or fragment thereof is produced in response to said peptide or antigen;

b) adding a labeled free PSA to said resulting test sample-antibody mixture of step (a); and c) determining the amount of PSA in the test sample by assessing the amount of competition between the PSA in the test sample and the labeled free PSA.

12. The method of claim 11 wherein, if free PSA is to be detected, said antibody of step (a) binds specifically to free PSA, and if total PSA is to be detected, said antibody of step (a) binds to total PSA.

13. A kit for determining the presence of PSA in a test sample comprising a container containing an antibody produced in response to immunization by a peptide selected from the group consisting of ABT2, ABT6, ABT1, ABT7, and ABT16.

14. A kit for determining the presence of PSA in a test sample comprising:

a) an antibody or fragment thereof which specifically binds to at least one site on PSA wherein said antibody or fragment thereof is produced in response to immunization by a peptide consisting essentially of an amino acid sequence of approximately 10–20 residues wherein said sequence is identical to the amino acid sequence of a region of PSA and consists essentially of one or more amino acids non-identical to the amino acid sequence of hk2, wherein said peptide is selected from the group consisting of ATB2, ABT6, ABT1, ABT7, and ABT16; and b) a probe antibody wherein said probe binds to a second site on said PSA.

15. A kit for determining the presence of free PSA in a test sample comprising:

a) an antibody or fragment thereof which specifically binds to a peptide comprising an amino acid sequence of approximately 10–20 residues wherein said sequence is identical to the amino acid sequence of a region of PSA and comprises one or more amino acids non-identical to the amino acid sequence of hk2, wherein said peptide is ABT6and wherein said antibody of fragment thereof has been produced in response to said peptide or antigen; and b) labeled free PSA.

* * * * *

UNITED STATES PATENT AND TRADEMARK OFFICE
CERTIFICATE OF CORRECTION

PATENT NO. : 6,143,509
DATED : November 7, 2000
INVENTOR(S) : Barry Lee Dowell et al.

It is certified that error appears in the above-identified patent and that said Letters Patent is hereby corrected as shown below:

Column 24,
Line 30, replace "wherein said peptide is ABT6and wherein" with -- wherein said peptide is ABT6 and wherein --.
Line 31, replace "antibody of fragment thereof" with -- antibody or fragment thereof --

Signed and Sealed this

Fifth Day of March, 2002

Attest:

Attesting Officer

JAMES E. ROGAN
Director of the United States Patent and Trademark Office